United States Patent
Wilfley et al.

(10) Patent No.: US 8,520,800 B2
(45) Date of Patent: Aug. 27, 2013

(54) METHOD AND APPARATUS FOR RADIATION RESISTANT IMAGING

(75) Inventors: Brian Patrick Wilfley, Los Altos, CA (US); Edward Gerald Solomon, Menlo Park, CA (US); Joseph Anthony Heanue, Oakland, CA (US)

(73) Assignee: Triple Ring Technologies, Inc., Newark, CA (US)

( * ) Notice: Subject to any disclaimer, the term of this patent is extended or adjusted under 35 U.S.C. 154(b) by 309 days.

(21) Appl. No.: 12/852,657

(22) Filed: Aug. 9, 2010

(65) Prior Publication Data

US 2012/0033790 A1 Feb. 9, 2012

(51) Int. Cl.
*A61N 5/10* (2006.01)

(52) U.S. Cl.
USPC .............................. 378/65; 378/203

(58) Field of Classification Search
USPC ...... 378/63, 65, 4–20, 160, 203; 250/363.04, 250/363.1, 515.1, 505.1
See application file for complete search history.

(56) References Cited

U.S. PATENT DOCUMENTS

| | | | |
|---|---|---|---|
| 5,550,378 A | 8/1996 | Skillicorn et al. | |
| 5,610,967 A | 3/1997 | Moorman et al. | |
| 5,644,612 A | 7/1997 | Moorman et al. | |
| 5,651,047 A | 7/1997 | Moorman et al. | |
| 5,682,412 A | 10/1997 | Skillicorn et al. | |
| 5,729,584 A | 3/1998 | Moorman et al. | |
| 5,751,785 A * | 5/1998 | Moorman et al. | 378/146 |
| 5,808,306 A | 9/1998 | Skillicorn et al. | |
| 5,835,561 A | 11/1998 | Moorman et al. | |
| 5,859,893 A | 1/1999 | Moorman et al. | |
| 6,060,713 A | 5/2000 | Skillicorn et al. | |
| 6,118,853 A | 9/2000 | Hansen et al. | |
| 6,118,854 A | 9/2000 | Solomon et al. | |
| 6,157,703 A | 12/2000 | Solomon et al. | |
| 6,175,611 B1 | 1/2001 | Melen et al. | |
| 6,178,223 B1 | 1/2001 | Solomon et al. | |
| 6,181,764 B1 | 1/2001 | Solomon et al. | |
| 6,183,139 B1 | 2/2001 | Solomon et al. | |
| 6,198,802 B1 | 3/2001 | Elliott et al. | |
| 6,208,709 B1 | 3/2001 | Melen | |
| 6,234,671 B1 | 5/2001 | Solomon et al. | |
| 6,649,914 B1 | 11/2003 | Moorman et al. | |
| 6,661,865 B1 * | 12/2003 | Popilock | 378/19 |
| 7,062,006 B1 | 6/2006 | Solomon et al. | |
| 2009/0274269 A1 * | 11/2009 | Foland et al. | 378/54 |
| 2009/0310738 A1 * | 12/2009 | Tischenko et al. | 378/10 |

* cited by examiner

*Primary Examiner* — Hoon Song
(74) *Attorney, Agent, or Firm* — Sabrina N. David

(57) ABSTRACT

The present invention pertains to an apparatus and method for radiation resistant medical imaging. A scanning beam x-ray source and x-ray detector are used. A detector shield is utilized to shield the x-ray detector from radiation.

13 Claims, 12 Drawing Sheets

METHOD AND APPARATUS FOR RADIATION RESISTANT IMAGING

FIELD OF THE INVENTION

The present invention relates to medical imaging. More particularly, the present invention pertains to a method and apparatus for radiation resistant x-ray imaging.

BACKGROUND

Radiation is frequently used to treat cancer tumors. For treating localized cancers such as tumors, the goal is to maximize the radiation level at the tumor and minimize radiation damage to the rest of the body. This is achieved by irradiating the tumor with a narrow beam of radiation aimed at the tumor from many different angles so as to maximize the radiation at the tumor while sparing surrounding healthy tissue.

Prior to radiation treatment, the patient will usually receive a computed tomography (CT) scan to diagnose and locate the tumor and also to provide the anatomical information necessary to develop a treatment plan. A treatment plan consists of a series of positions for the radiation therapy source relative to the patient that will produce the desired radiation distribution centered on the tumor in the patient. Each position of the radiation therapy source may have different radiation energy levels, durations, and control of the profile of the radiation therapy beam.

It is critically important that the location of the tumor be accurately known so that the planned radiation distribution can be aligned with the tumor. If the radiation distribution is not accurately aligned with the tumor, the tumor will not receive a sufficient radiation level to damage or kill the tumor and healthy organs may receive damaging levels of radiation.

A radiation treatment system may have a linear accelerator radiation source and an x-ray imaging system consisting of an x-ray source and a large-area x-ray detector. These can be attached to a rotating mechanical gantry. By rotating the gantry around the patient, many two-dimensional x-ray projection views through the patient can be obtained and a three-dimensional cone-beam CT image can be reconstructed showing the tumor and other anatomical landmarks.

The x-ray source and large-area detector can be arranged approximately at right angles to the radiation therapy beam. This is done to avoid direct radiation from the linear accelerator striking these components, which can be damaged by the high radiation levels from the linear accelerator.

A number of real-time x-ray imaging systems are known. These include fluoroscope-based systems where x-rays are projected into an object to be x-rayed and shadows caused by relatively x-ray opaque matter within the object are displayed on the fluoroscope located on the opposite side of the object from the x-ray source. Scanning x-ray tubes have been known in conjunction with the fluoroscopy art since at least the early 1950s. Moon, Amplifying and Intensifying the Fluoroscopic Image by Means of a Scanning X-ray Tube, Science, Oct. 6, 1950, pp. 389-395.

Reverse-geometry scanning beam x-ray imaging systems are also known. In such systems, an x-ray tube is employed to generate x-ray radiation. Within the x-ray tube, an electron beam is generated and focused upon a small spot on the relatively large anode (transmission target) of the tube, inducing x-ray radiation emission from that spot. The electron beam is deflected (electromagnetically or electrostatically) in a raster scan pattern over the anode. A small x-ray detector is placed at a distance from the anode of the x-ray tube. The detector typically converts x-rays which strike it into an electrical signal in proportion to the detected x-ray flux. When an object is placed between the x-ray tube and the detector, x-rays are attenuated by the object in proportion to the x-ray density of the object. While the x-ray tube is in the scanning mode, the signal from the detector is inversely proportional to the x-ray density of the object.

Examples of known reverse-geometry scanning beam x-ray systems include those described in U.S. Pat. Nos. 3,949,229; 4,032,787; 4,057,745; 4,144,457; 4,149,076; 4,196,351; 4,259,582; 4,259,583; 4,288,697; 4,321,473; 4,323,779; 4,465,540; 4,519,092; and 4,730,350.

In a typical known embodiment of a reverse-geometry scanning beam system, an output signal from the detector is applied to the z-axis (luminance) input of a video monitor. This signal modulates the brightness of the viewing screen. The x and y inputs to the video monitor are typically derived from the signal that effects deflection of the electron beam of the x-ray tube. Therefore, the luminance of a point on the viewing screen is inversely proportional to the absorption of x-rays passing from the source, through the object, to the detector.

What are needed are a radiation therapy system and an imaging system capable of producing rapid high quality images. Furthermore, the imaging system should provide low radiation imaging and be protected from the radiation source.

SUMMARY

The present invention pertains to an apparatus and method for radiation resistant medical imaging. A radiation therapy source for delivering radiation to a target in a human patient and a scanning beam x-ray source for providing x-ray photons directed to the target are used. A x-ray detector is used for measuring the number of x-ray photons passing through the target and striking the detector and an image reconstruction processor is used for producing an image based on the number of x-ray photons passing through the target and striking the detector. A detector shield is positioned between the x-ray detector and the radiation therapy source for shielding the x-ray detector from the radiation from the radiation therapy source. A method for delivering radiation therapy to a human patient is also described. An electron beam is scanned over a target to produce x-ray photons and the x-ray photons are directed towards an object in the patient. The amount of x-ray photons striking a detector is measured and an image of the object is produced based on the amount of x-ray photons striking the detector. Radiation from a radiation therapy source is directed towards the object and the detector can be shielded from the radiation.

These and other objects and advantages of the various embodiments of the present invention will be recognized by those of ordinary skill in the art after reading the following detailed description of the embodiments that are illustrated in the various drawing figures.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

Figure 1:
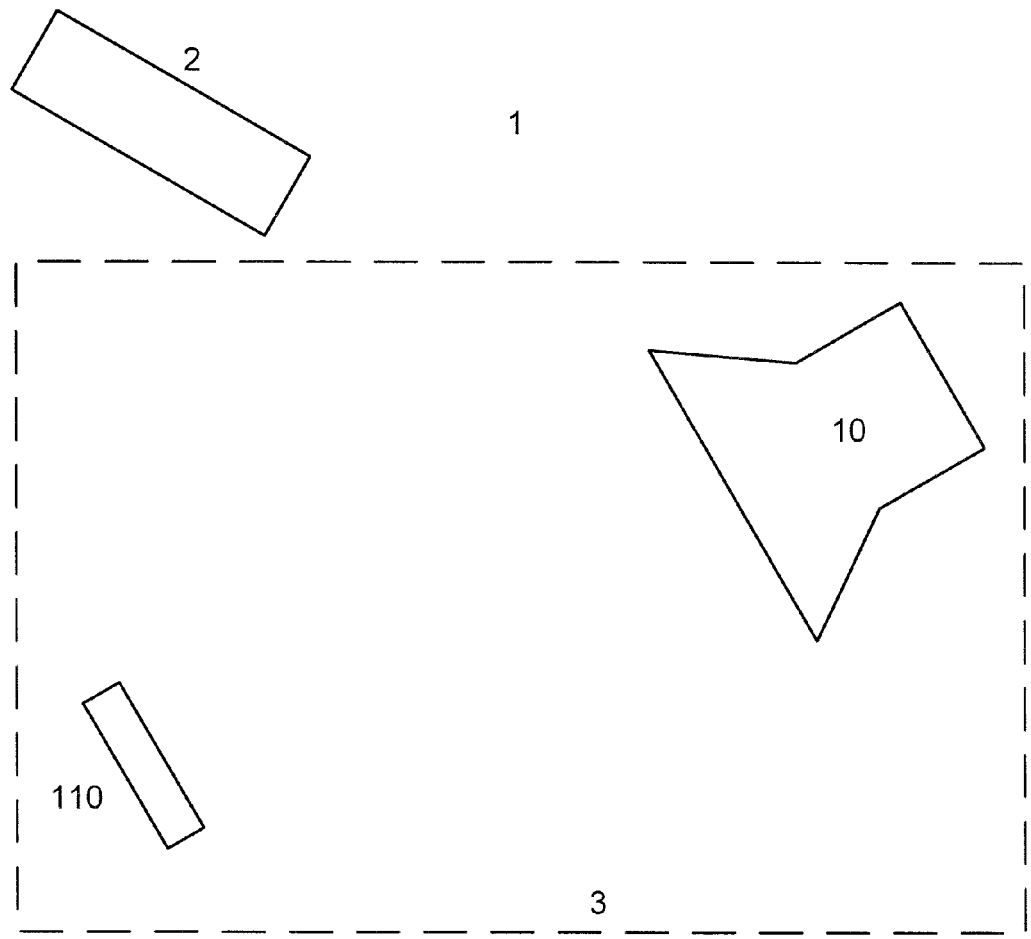
FIG. 1 is a diagram showing an exemplary radiation therapy system of one embodiment of the present invention.

FIG. 1 is a diagram showing an exemplary radiation therapy system of one embodiment of the present invention. Radiation therapy system 1 comprises radiation source 2 and imaging system 3. Radiation source 2 can be a particle accelerator, x-ray source, radioisotope source or other radiation source. Radiation source 2 can have an energy of 0.5 MeV, 1 MeV, 1.5 MeV, 2 MeV, 3 MeV, 4 MeV, 5 Mev, 6 MeV, 7 MeV, 8 MeV, 9 MeV, 10 MeV, 11 MeV, 12 MeV, 13 MeV, 14 MeV, 15 MeV, 16 MeV, 17 MeV, 18 MeV, 19 MeV, 20 MeV, 21 MeV, 22 MeV, 23 MeV, 24 MeV, 25 MeV, 26 MeV or any energies in between such energies or any range of energies in between such energies. Imaging system 3 can be an x-ray imaging system, nuclear medicine imaging system, gamma camera imaging system, positron-annihilation-radiation imaging system, PET imaging system, SPECT imaging system, ultrasound imaging system or other imaging system. An imaging system is disclosed in commonly owned U.S. Pat. Nos. 5,651,047, 6,183,139, 6,198,802 and 6,234,671, entitled "Maneuverable and Locateable Catheters," X-Ray Scanning Method and Apparatus," "Scanning Beam X-Ray Source and Assembly," "X-Ray System with Scanning Beam X-Ray Source Below Object Table," respectively, all of which are incorporated herein by reference in their entirety. Imaging system 3 can further comprise source 10 and detector 110. Since imaging system 3 is in relative close proximity to radiation source 2, components in imaging system 3 including source 10 and detector 110 can be damaged by radiation from radiation source 2.

Figure 2:
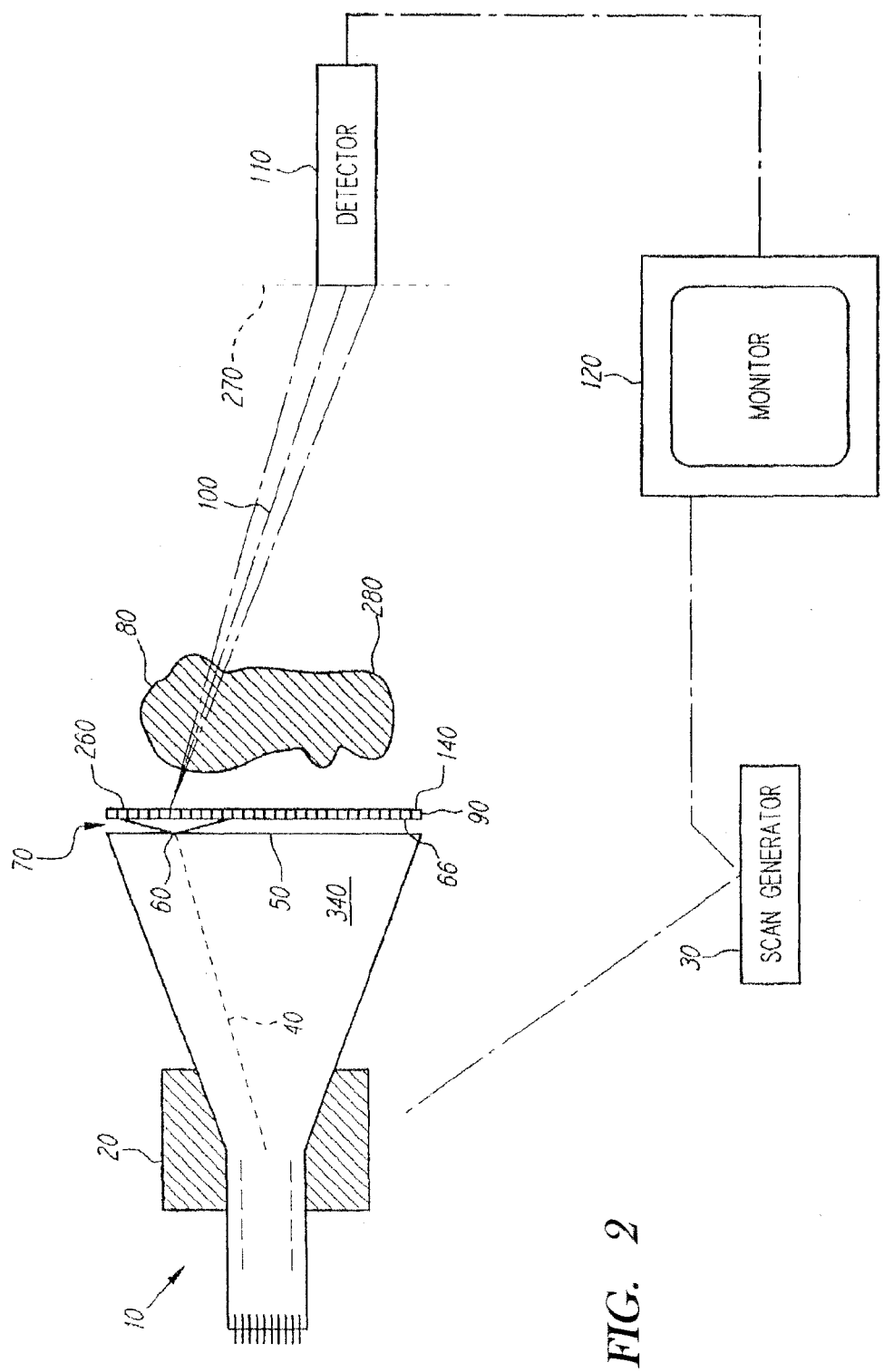
FIG. 2 is a diagram showing an exemplary scanning-beam x-ray imaging system of one embodiment of the present invention.

FIG. 2 is a diagram showing an exemplary scanning-beam x-ray imaging system of one embodiment of the present invention. The scanning-beam x-ray imaging system can comprise scanning x-ray source 10. X-ray source 10 can be the x-ray source described more fully in commonly owned U.S. Pat. Nos. 5,682,412 and 6,198,802, entitled "X-Ray Source" and Scanning Beam X-Ray Source and Assembly" respectively, all of which are hereby incorporated herein by reference in their entirety. To resist damage from radiation coming from radiation source 2, the vacuum envelope and electron gun in x-ray source 10 can be made of metal structures with insulator elements for electrical isolation. The insulator elements can be ceramic, glass or other insulator materials.

Use of scanning x-ray source 10 allows for utilization of a reverse geometry configuration for imaging system 3. In a reverse geometry configuration, a smaller detector can be used whereas a point source requires a much larger detector. The area of the detector can be 2, 3, 4, 5, 6, 7, 8, 9, 10, 11, 12, 13, 14, 15, 16, 17, 18, 19 or 20 percent of the area of the maximum field of view for given source configuration and detector distance from patient or any percentage in between such percentages or any range of percentages in between such percentages. A smaller detector allows the use of a smaller, light and more maneuverable shield. A smaller detector also decreases the amount of detector area subjected to radiation directly or scattered from radiation source 2 decreasing the susceptibility of the detector to radiation damage. A smaller detector also allows greater flexibility in positioning the detector with respect to the patient and radiation source 2.

In a reverse geometry configuration, the detector can also be located further away from the patient than a detector with a point x-ray source. With a point x-ray source, the size of the detector required for a given maximum field of view size increases with the distance of the detector from the patient. The already large detector required with a point x-ray source becomes even larger with increasing distance. With a scanning x-ray source in a reverse geometry configuration, the size of the detector required for a given maximum field of view size decreases with the distance of the detector from the patient. Thus, the detector for scanning x-ray source 10 can be located with a distance from the patient of 1.3 m, 1.4 m, 1.5 m, 1.6 m 1.7 m, 1.8 m, 1.9 m, 2 m, 2.1 m 2.2 m, 2.3 m, 2.4 m, 2.5 m or any distance in between such distances or any range of distances in between such distances.

X-ray source 10 can comprise deflection yoke 20 under the control of scan generator 30. Deflection yoke 20 can comprise one or more magnetic focus or deflection coils. The magnetic focus or deflection coils can be made with insulated electrical wire wound around a core. To resist damage from radiation coming from radiation source 2, the electrical wire can be copper, aluminum or other conductor. The core can be ferrite, steel, iron or other magnetic alloy. The insulation material on the electrical wire can be a radiation resistant material. The insulation material on the electrical wire can be silicon rubber or polyimide.

To resist damage from radiation coming from radiation source 2, scan generator 30, the electron gun and other electronic components including electronic components that control x-ray source 10 can be shielded from radiation coming from radiation source 2. Electronic components can also be selected that are robust under radiation exposure or low susceptibility to radiation damage. Shielding can be tungsten, tungsten copper, tungsten alloy, lead, lead alloy, lead antimony, tantalum, tantalum alloy or other material with high Z atomic number. Thickness of shielding can be 0.5 cm, 1 cm, 2 cm, 3 cm, 4 cm, 5 cm, 6 cm, 7 cm, 8 cm, 9 cm, 10 cm, 11 cm, 12 cm, 13 cm, 14 cm, 15 cm or any thickness in between such thicknesses or any range of thicknesses in between such thicknesses. Shielding can also be a hollow housing with shielding material inside. Shielding material can be tungsten, tungsten copper, tungsten alloy, lead, lead antimony, lead alloy, tantalum, tantalum alloy or other material with high Z atomic number and can be in pellet form, powder form or other form. In addition, the housing of x-ray source 10 can be used as a shield from radiation. The housing can be made from tungsten, tungsten copper, tungsten alloy, lead, lead alloy, lead antimony, tantalum, tantalum alloy or other material with high Z atomic number. Thickness of housing can be 0.5 cm, 1 cm, 2 cm, 3 cm, 4 cm, 5 cm, 6 cm, 7 cm, 8 cm, 9 cm, 10 cm, 11 cm, 12 cm, 13 cm, 14 cm, 15 cm or any thickness in between such thicknesses or any range of thicknesses in between such thicknesses. Deflection yoke 20, scan generator 30, the electron gun or other electronic components including electronic components that control x-ray source 10 can be located behind the housing such that the housing is between the patient and deflection yoke 20, scan generator 30, the electron gun or other electronic components including electronic components that control x-ray source 10. The electron gun can also be located at the back end of x-ray source 10 with a distance from the side of x-ray source 10 facing the patient of 14 inches, 15 inches, 16 inches, 17 inches, 18 inches or any distance in between such distances or any range of distances in between such distances.

Scan generator 30 and other electronic components including electronic components that control x-ray source 10 can also be shielded by locating them outside the shielded bunker used to contain the patient treatment system. In this arrangement, some of the interconnections between the x-ray source 10, scan generator 30 or the electronic components outside the bunker may be exposed to high levels of radiation from the radiation source 2. Electrical wiring or fiberoptic interconnections can be selected that are rated by their manufacturer for operation in high radiation environments. These interconnections can be shielded by appropriate thicknesses of high-density materials. The high density materials can be tungsten, tungsten copper, tungsten alloy, lead, lead antimony, lead alloy, tantalum, tantalum alloy or other material with high Z atomic number. Thickness of shielding can be 0.5 cm, 1 cm, 2 cm, 3 cm, 4 cm, 5 cm, 6 cm, 7 cm, 8 cm, 9 cm, 10 cm, 11 cm, 12 cm, 13 cm, 14 cm, 15 cm or any thickness in between such thicknesses or any range of thicknesses in between such thicknesses.

An electron beam 40 generated within x-ray source 10 can be scanned across target 50 within x-ray source 10 in a predetermined pattern. Target 50 can be a grounded anode target. The predetermined pattern can be a raster scan pattern, a serpentine (or "S" shaped) pattern, a spiral pattern, a random pattern, a gaussian distribution pattern centered on a predetermined point of the target, or such other pattern as may be useful to the task at hand. The serpentine (or "S" shaped) pattern can eliminate the need in a raster scan pattern for horizontal "fly back."

As electron beam 40 strikes target 50 at focal spot 60, a cascade of x-rays 70 is emitted and travel outside of x-ray source 10 toward the object 80 to be imaged. To optimize system performance of the present embodiment, a cone of x-ray photons can be generated that will diverge in a manner that will just cover the multi-detector array 110. The detector including multi-detector array 110 is further described in commonly owned U.S. Pat. No. 5,808,306, entitled "X-ray Detector," which is hereby incorporated herein by reference in its entirety.

This divergence can be accomplished by placing a collimating assembly between the target 50 of the scanning x-ray source 10 and the multi-detector array 110, and can be between the target 50 and the object to be imaged. The collimating assembly can be a collimation grid 90, comprising a grid of x-ray transmissive apertures 140. Collimation grid 90 can be designed to permit passage of only those x-ray pencil beams 100 whose axes lie in a path that directly intercepts multi-detector array 110. Collimation grid 90 can be stationary with respect to multi-detector array 110 while the system is in operation. Thus, as electron beam 40 is scanned across target 50, at any given moment there is only a single x-ray pencil beam 100 which passes through object 80 to multi-detector array 110.

To resist damage from radiation coming from radiation source 2, collimation grid 90 can be made of metal structures. The metal structures can be tungsten, tungsten copper, tungsten alloy, lead, lead antimony, lead alloy, tantalum, tantalum alloy or other material with high Z atomic number.

The output of multi-detector array 110 can be processed and displayed on monitor 120 as luminance values. Image processing techniques can be used to produce a computer driven image on an appropriate display or photographic or other medium.

The imaging system disclosed herein is a low exposure system in that it can expose the patient at a rate of about 0.09 to 0.33 R/min with a 30 frame/sec refresh rate measured at the entrance to the patient, which in other systems under the same conditions can typically be between 2.0 to 2.8 R/min. Whole body exposure with a 30 frame/sec refresh rate can be lower as well.

Collimation grid 90 can comprise an array of apertures 140, the axes of each, are oriented or pointed toward multi-detector array 110. That is to say that the axes of apertures within the collimation grid 90 are not parallel to each other and form an acute to the line perpendicular to the output face 260 of the collimation grid 90. For example, a collimation grid for chest imaging can comprise apertures forming an angle with a line perpendicular to the output face 260 of the collimation grid 90 of between 0 degree at the center of the collimation grid 90 to as much as 20 degrees at the edge of the grid 90. A breast imaging application on the other hand can have a collimation grid 90 comprising apertures forming an angle with a line perpendicular to the output face 260 ranging to 45 degrees at the edge of the grid. Thus, a different collimation grid 90 can be selected and inserted for use in different imaging applications.

The number of apertures 140 in collimation grid 90 can correspond to the number of image pixels to be generated. For example, 500 by 500 to 1024 by 1024. Alternatively, the image pixel to aperture ratio can be increased, i.e., fewer apertures than image pixels may be used, in conjunction with the technique of "sub-sampling." The system spatial resolution can be determined, in part, by the pitch of the apertures in collimation grid 90. The precise number of apertures suggested above is illustrative only, and is not intended in any way to be limiting.

The x-ray absorbent portion of preferred collimation grid 90 can be designed to absorb errant x-rays so that they do not illuminate object 80. This can be accomplished by fabricating collimation grid 90 with sufficient thickness so that the x-ray radiation passing through an aperture 140 towards the multi-detector array 110 is substantially greater than the cumulative x-ray radiation passing through the x-ray absorbent portion in all directions other than toward multi-detector array 110. Such errant x-rays would provide the object 80 and attending staff with x-ray dosage but contribute no meaningful information to the image.

Square apertures 140 can be used and can be 0.0381 cm (0.015 in) by 0.0381 cm in dimension while round apertures can be 0.015 in (0.038 cm) in diameter. Both square and round apertures can yield a cross sectional area at multi-detector 110 that can be about $\frac{1}{100}$ the cross sectional area of other detectors. The cross sectional area of the face of the multi-detector array 110 can be much smaller than in other conventional systems. As a result, x-rays scattered at the object miss the multi-detector array and do not tend to fog the image as they do in other conventional systems which typically utilize relatively large surface area detectors.

Figure 3:
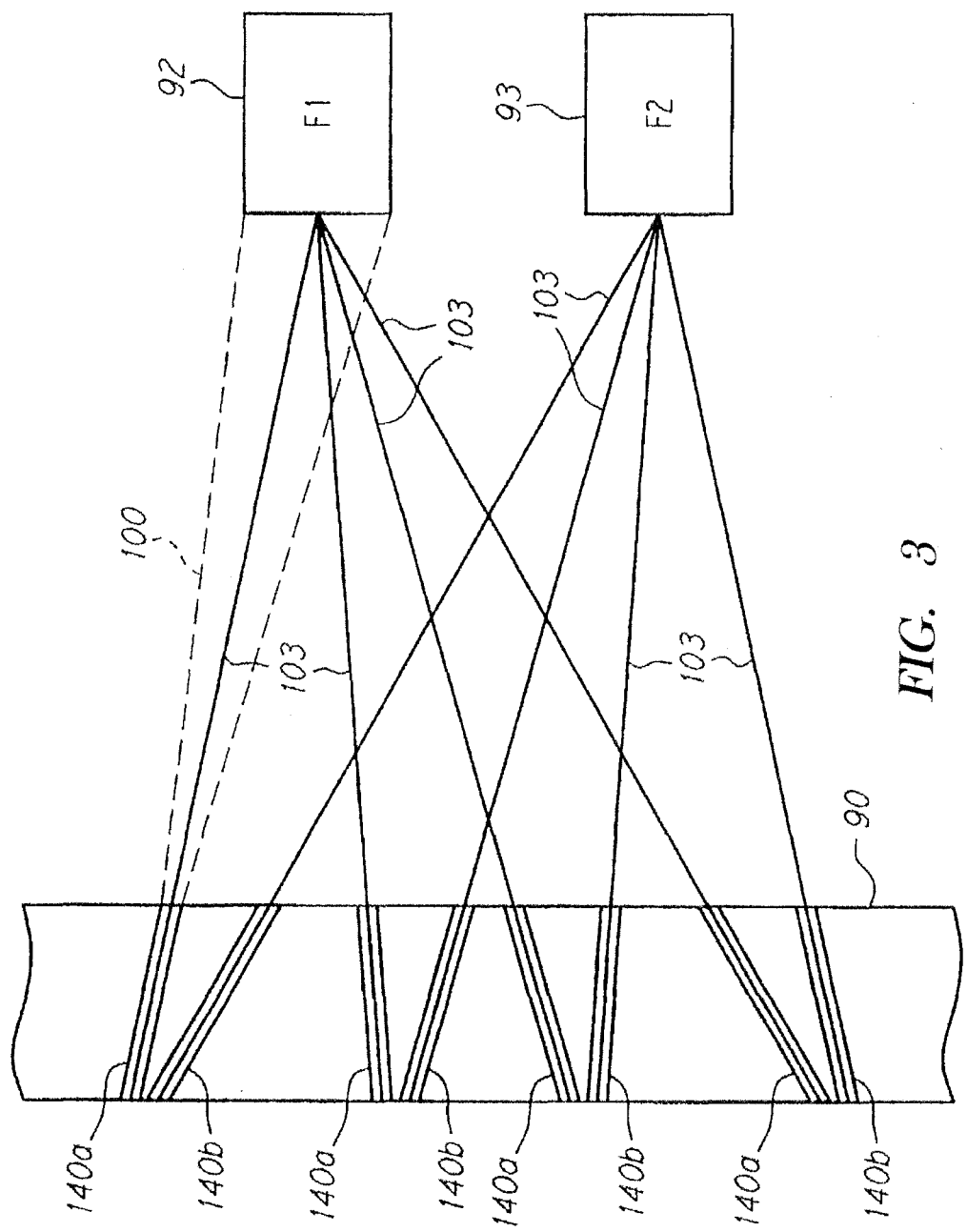
FIG. 3 is a diagram showing an exemplary scanning-beam x-ray imaging system of one embodiment of the present invention with a collimation grid having a plurality of focal points to obtain stereoscopic x-ray images.

FIG. 3 is a diagram showing an exemplary scanning-beam x-ray imaging system of one embodiment of the present invention with a collimation grid having a plurality of focal points to obtain stereoscopic x-ray images. The axes 103 of the x-ray pencil beams 100, corresponding to the aperture axes of every other row of apertures 140a in grid 90 can be pointed at focal point F1 at the center of multi-detector array 92 and the aperture axes of the remaining apertures are pointed at focal point F2 at the center of multi-detector array 93. One can scan the apertures in a raster or serpentine pattern and create a "line" of data from the first multi-detector array, and a line of data from the second multi-detector array. Repeating this, it is possible to build up two complete images, as seen from two distinct angles and thereby display them with conventional stereoscopic imaging display systems to provide a stereoscopic x-ray image.

Apertures 140a, 140b can diverge from a common first aperture 140 to form a "V" as shown providing separate paths along the "legs" of the "V" for x-ray pencil beams 100. There is no requirement, however, that apertures 140a, 140b diverge from a common aperture as shown, but an advantage of the "V"-shaped aperture where the x-rays enter at the common aperture or apex of the "V" is that both multi-detector arrays 92 and 93 can be illuminated simultaneously, the "V" acting as an x-ray splitter with some of the x-rays going to multi-detector array 92 and some to multi-detector array 93. This can decrease by 50% the power required for the beam current.

To achieve resolutions of several line pairs per millimeter or more at the object plane, the spatial resolution limit in some reverse-geometry systems is in large part determined by the size of the single non-segmented detector. Generally speaking, a small non-segmented detector can provide high spatial resolution while a large non-segmented detector provides high collection efficiency. This trade-off can be a problem in developing low dosage x-ray imaging systems.

When such a detector is small to increase resolution, a large proportion of the x-rays emitted by target 50 are unused by the single detector even when a collimator grid 90 is used. This is, in fact, how industrial reverse-geometry scanning-beam x-ray inspection systems are designed, where dose is usually not a consideration. Accordingly, while one can decrease the size of a detector by placing, for example, a lead washer in front of the single detector and thereby increase spatial resolution, the x-ray intensity and/or exposure time would have to be increased to maintain contrast resolution.

By fabricating a multi-detector array having a large area subdivided into multiple smaller detector array elements, a large capture area is achieved, while simultaneously through image reconstruction techniques retaining an image resolution that is comparable to the size of a single small detector element without increasing x-ray intensity and/or exposure time.

Figure 4:
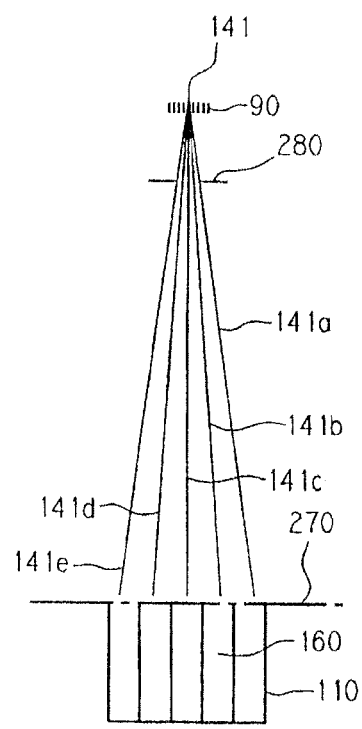
FIG. 4 is a diagram showing a single x-ray beam and generation of information for 5 image pixels.
Figure 5:
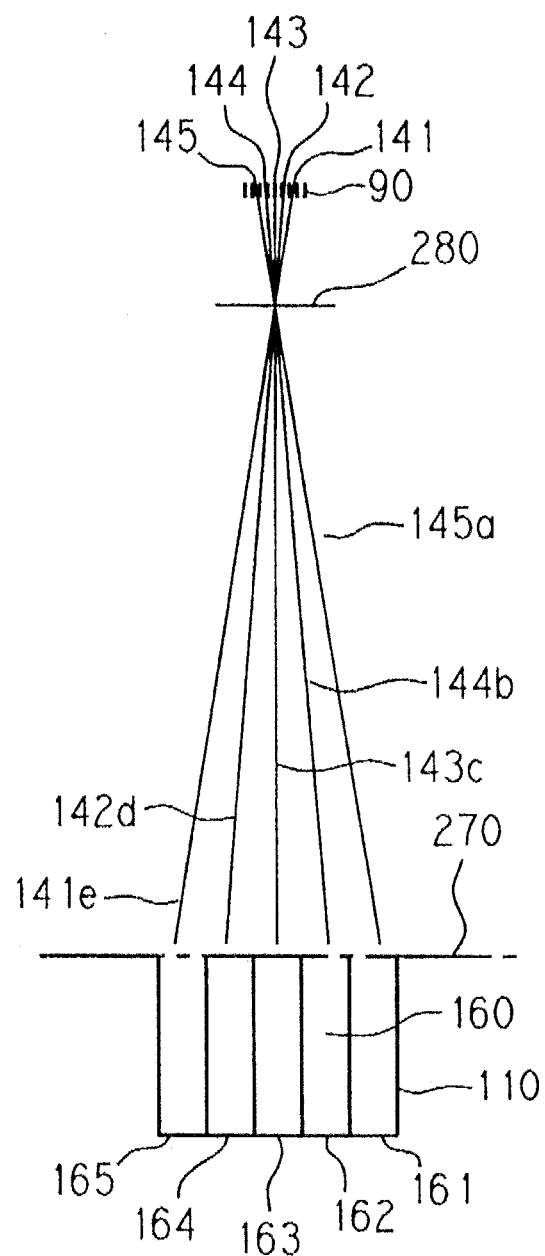
FIG. 5 is a diagram showing the sequential positions of the axes of x-ray micro-beams from x-ray pencil beams emanating from five consecutive apertures illuminating a single image pixel

The resolution defined by the individual detector elements is maintained by distributing and summing the outputs from the individual detector elements into a memory buffer in which each address, i.e., image pixel, corresponds to a specific location in the object plane 280. As an electron beam 40 is moved discretely across the target 50, illuminating the area behind selected apertures 140 of the collimation grid 90, the address, to which the output of a given individual detector element is added, changes. The imaging geometry is shown in FIGS. 4 and 5. In FIG. 4, a single x-ray beam 100 is shown along with how it generates information for 5 image pixels. Effectively, the single x-ray pencil beam 100 emanating from individual aperture 141 is divided into x-ray micro-beams, the number of x-ray micro-beams created corresponding to the number of individual detector elements 160 which comprise the multi-detector array 110. In the case shown in FIG. 4, the axes of five x-ray micro-beams 141a, 141b, 141c, 141d and 141e are shown. In FIG. 5, the sequential positions of the axes of the x-ray micro-beams from x-ray pencil beams 100 emanating from five consecutive apertures 141 through 145 illuminating a single image pixel ("IP") are shown. The outputs from the five individual detector elements 161, 162, 163, 164 and 165 receiving the x-ray flux from the five x-ray micro-beams, 145a, 144b, 143c, 142d and 141e respectfully, are added together to provide the luminance for the single pixel IP.

Stated differently, the output for each of the individual detector elements 160 is stored for later summation in an image buffer, at a memory address that corresponds to a very small specific region in the object plane 280, e.g., a single image pixel.

Accordingly, in one embodiment the memory storage address for the output of each individual detector element 160 changes with the position of the scanning x-ray beam 40 in an ordered fashion such that each memory address contains the sum of the radiation passing through a specific image pixel or spot in the object plane 280. In this way the spatial resolution of the system is determined by the size of a single individual detector element 160, while the contrast resolution of the system is determined by the area of all of the individual detector elements comprising the multi-detector array 110.

Figure 6:
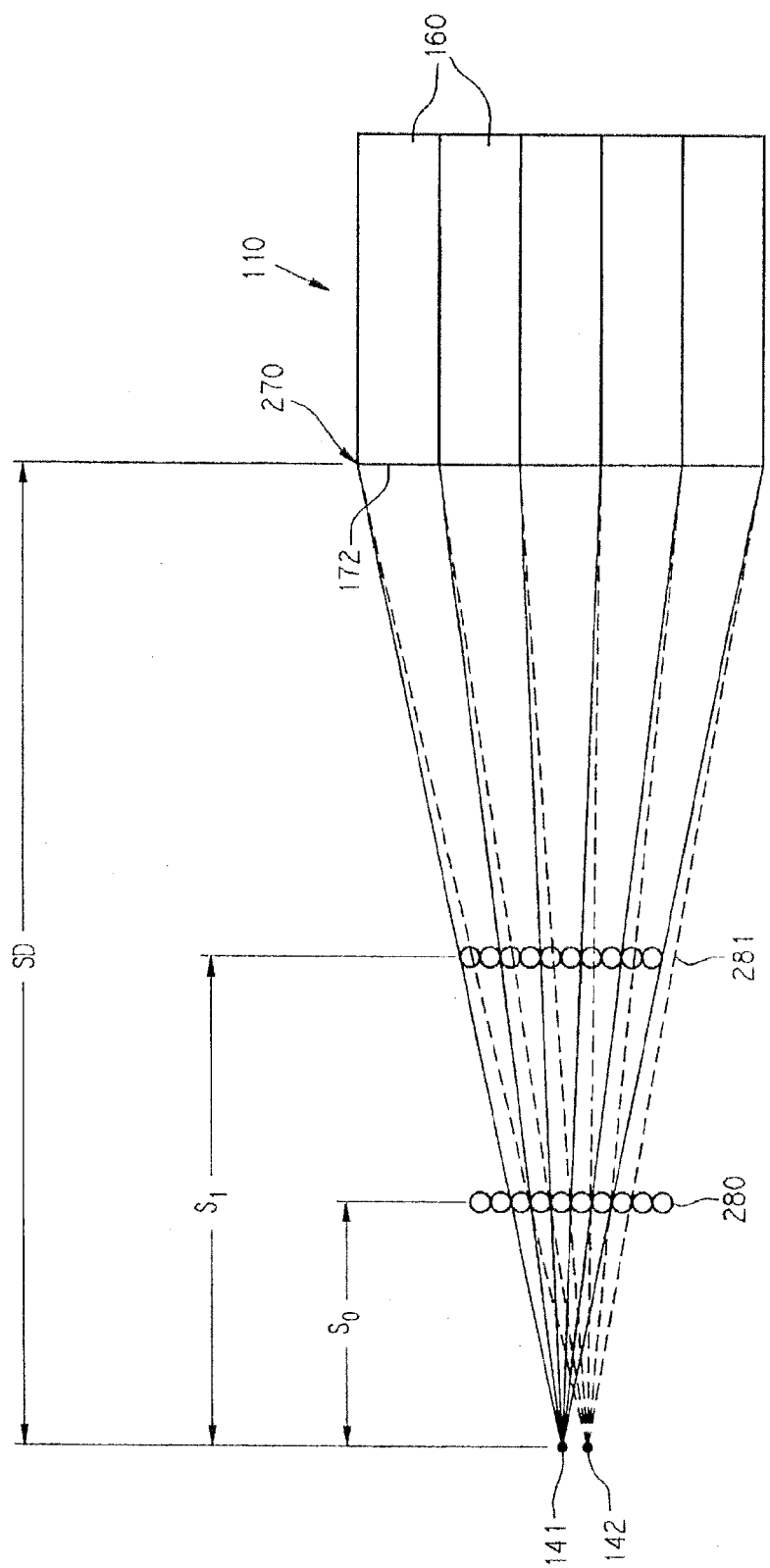
FIG. 6 is a diagram showing X-ray pencil beams from a first aperture and a second aperture passing through an object plane a distance $S_0$ from the apertures and passing through a plane a distance $S_1$ from the apertures.

An additional benefit of this multi-detector array imaging geometry is that the depth of field of the object plane 280 is narrowly defined. Structures lying in front of or behind it will be blurred (out of focus). X-ray pencil beams from a first aperture 141 and a second aperture 142 are depicted in FIG. 6 passing through an object plane 280 a distance $S_0$ from apertures 141,142 and passing through a plane 281 a distance $S_1$ from apertures 141, 142 where $S_1 > S_0$. The bubbles represent image pixels $IP_1$ through $IP_0$. As can be readily seen, the resolution at $S_1$ is less than that available at $S_0$. This feature provides for improved localization and visualization of detailed structures in the plane of interest 280, while providing an adequate depth of field that may be modified by the system geometry.

Conventional image intensifier technology typically has basic constraints that limit a system's sensitivity. A scanning-beam x-ray imaging system can result in the subject under examination being exposed to the lowest possible level of x-rays commensurate with achieving image quality adequate to meet the requirements of the procedure being performed. This means that the system used to detect the x-ray photons emerging from the subject preferably has the highest possible detective quantum efficiency. To achieve this, the scintillating material used in the individual detector elements preferably has a length in the direction in which the x-ray photons travel that is sufficient to ensure that no x-ray photons emerge from the end opposite the incident x-rays, i.e., the x-ray photon energy should be adequately dissipated in the material to maximize the output of the detector.

There are several types of individual detector elements which can be used in the scanning-beam x-ray imaging system. Semiconductor detectors using silicon, selenium, cadmium telluride, cadmium zinc telluride, or other materials can be used. Scintillators or optical detectors can also be used, for example, cesium iodide or cadmium tungstate scintillators with amorphous-silicon, CMOS, or CCD optical detectors. A scintillator in which x-ray photon energy is converted to visible light energy and the light intensity is then converted to an electrical signal by means of a photomultiplier, photo diode, CCD or similar device can be utilized. Because the information from each aperture must be obtained in a very short time period, the scintillating material should have a fast response and a minimum afterglow time. Afterglow is the phenomenon wherein the scintillator continues to emit light after the stimulating incident x-rays have ceased. Even faster response and shorter afterglow times are required if x-ray intensity measurements are obtained using the x-ray photon counting technique.

Use of the x-ray photon counting technique and photon counting detectors in high radiation environments can have additional advantages. One type of photon-counting detectors comprises detectors that convert incoming photons into charge carriers such as electrons or holes in a semiconductor material, or positive and negative ions in a gas or liquid material. An electric field applied to the material will sweep positive charges, such as positive ions or holes, towards one electrode and negative charges, such as negative ions or electrons, towards another electrode. As the charges accumulate on their respective electrodes, they form a current pulse. Such a current pulse can be analyzed using pulse-height analysis techniques to yield a count of the number of incoming photons.

With this type of photon counting detector, individual selected photons that strike the detector surface are counted by detecting a pulse of electrons or other charge carriers. The pulse of charge has significantly greater intensity than the charge detected between selected photons or when selected photons are absent. With an energy integrating detector, on the other hand, photons result in flow of electrons or other charge carriers and the detector measures the amount of charge over a period of time. The energy integrating detector does not count or detect individual photons. When the photon counting detector and energy integrating detector are subjected to high radiation, both will suffer damage caused by the radiation including increased leakage current and introduction of charge trapping defects such as dislocations. With an energy integrating detector, damage caused by the radiation will affect the amount of charge measured by the detector over a given period of time and introduce error in the measurement by the detector. However, with a photon counting detector, the detector counts and detects individual pulses, not charge over a period of time or measurement of charge over a period of time. When the photon counting detector experiences radiation damage, the amount of charge measured during the period without photons and during the period of the pulse or presence of photons may be affected but detection of the pulse and pulse counting remains unaffected unless radiation damage becomes so significant that the pulse is indistinguishable. In this manner, photon counting detectors can be more resistant to radiation damage than energy integrating detectors.

A second type of photon-counting detectors comprises detectors that convert an incoming photon into several optical photons which together form an optical pulse. The optical photons can be in the visible range with wavelengths approximately within the range of from 400 nm to 700 nm; infrared photons with wavelengths longer than approximately 700 nm; or ultraviolet photons with wavelengths shorter than 400 nm. The optical pulse can be detected with an optical detector such as a CCD, a photo-diode, or a photo-transistor, thereby transducing the optical pulse into an electrical pulse. The electrical pulse can be analyzed using pulse-height analysis techniques to yield a count of the number of incoming photons.

X-ray detectors require sensitive electronics to amplify the small electronic signals produced by the incident x-ray photons and x-ray detectors are generally more sensitive to radiation damage than x-ray source 10. It is desirable to protect the x-ray detectors from high levels of radiation from radiation source 2. The location of the x-ray detectors can be arranged so as to avoid direct illumination or reduce illumination by radiation source 2. In one embodiment of the present invention, x-ray detector 110 is coupled to radiation source 2. X-ray detector 110 can be coupled to radiation source 2 by a gantry. X-ray detector 110 can be located in such a manner that the angle between the line from radiation source 2 to the radiation target and the line from the center of x-ray detector 110 to the radiation target is 10, 20, 30, 40, 50, 60, 70, 80 degrees or any angle in between such angles or any range of angles in between such angles. The angle can be fixed by attaching x-ray detector 110 and radiation source 2 to a gantry. Alternatively, such angle between x-ray detector 110, radiation source 2 and the radiation target can vary due to rotation or movement of x-ray detector 110 or radiation source 2. Control methods can be implemented such that during activation of radiation source 2, the location of x-ray detector 110 or radiation source 2 is restricted so that such angle between the center of x-ray detector 110, radiation source 2 and the radiation target is 10, 20, 30, 40, 50, 60, 70, 80 degrees or any angle in between such angles or any range of angles in between such angles.

In addition, during patient treatment, there can be moderate levels of scattered radiation about the patient. This scattered radiation can be in all random directions. The x-ray detector can be shielded on those sides or surfaces of the detector assembly housing which do not receive x-ray photons used for imaging. This shielding can be fabricated from high-density materials such as tungsten, tungsten copper, tungsten alloy, lead, lead antimony, lead alloy, tantalum, tantalum alloy or other material with high Z atomic number. Thickness of shielding can be 0.5 cm, 1 cm, 2 cm, 3 cm, 4 cm, 5 cm, 6 cm, 7 cm, 8 cm, 9 cm, 10 cm, 11 cm, 12 cm, 13 cm, 14 cm, 15 cm or any thickness in between such thicknesses or any range of thicknesses in between such thicknesses.

Figure 7:
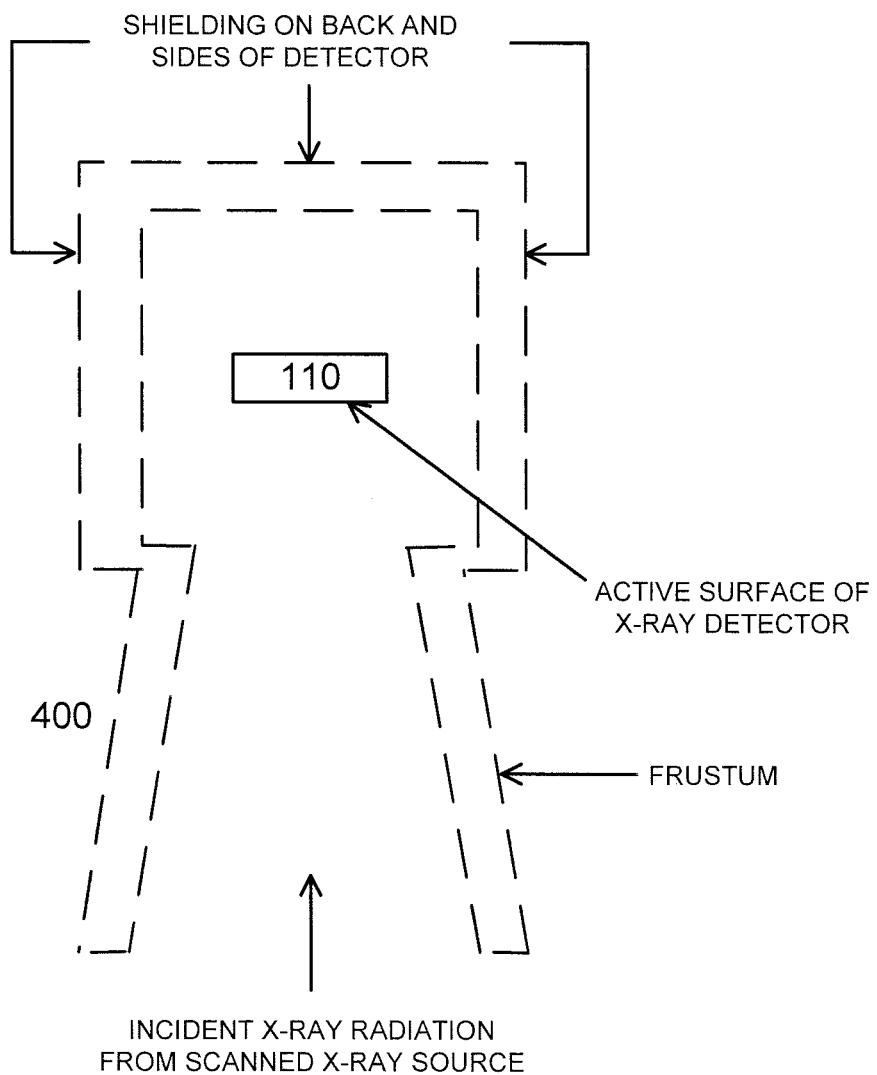
FIG. 7 is a diagram showing a detector shield of one embodiment of the present invention.

The active surface of x-ray detector 110 cannot be permanently shielded, as this would impair the functioning of x-ray detector 110 for its imaging purpose. The active surface of the x-ray detector 110 can be partially protected from scattered radiation. FIG. 7 is a diagram showing a detector shield of one embodiment of the present invention. Detector shield 400 can be shaped as conical frustum, elliptical frustum, square frustum, rectangular frustum, pentagon frustum, hexagon frustum, heptagon frustum, octagon frustum or other frustum.

Detector shield 400 is positioned with the narrow portion near x-ray detector 110 as shown in FIG. 7. The angular dimension of a side of detector shield 400 and the line normal to the smaller base of detector shield 400 can be 3, 4, 5, 6, 7, 8, 9, 10 degrees or any angle in between such angles or any range of angles in between such angles. The height of detector shield 400 can be 10 cm, 15 cm, 20 cm, 25 cm, 30 cm, 35 cm, 40 cm or any height in between such heights or any range of heights in between such heights. The dimension of the smaller base of detector shield 400 can match or be slightly larger than the dimensions of x-ray detector 110. If a conical frustum or elliptical frustum, the diameter of the smaller base of detector shield 400 can be 5 cm, 6 cm, 7 cm, 8 cm, 9 cm, 10 cm, 10.5 cm, 11 cm, 12 cm or any diameter in between such diameters or any range of diameters in between such diameters. If a square frustum, rectangular frustum, pentagon frustum, hexagon frustum, heptagon frustum, octagon frustum or other frustum, the height of the smaller base of detector shield 400 can be 5 cm, 6 cm, 7 cm, 8 cm, 9 cm, 10 cm, 10.5 cm, 11 cm, 12 cm or any or any height in between such heights or any range of heights in between such heights. Detector shield 400 does not interfere with the entry of x-ray photons from x-ray source 10.

Figure 8:
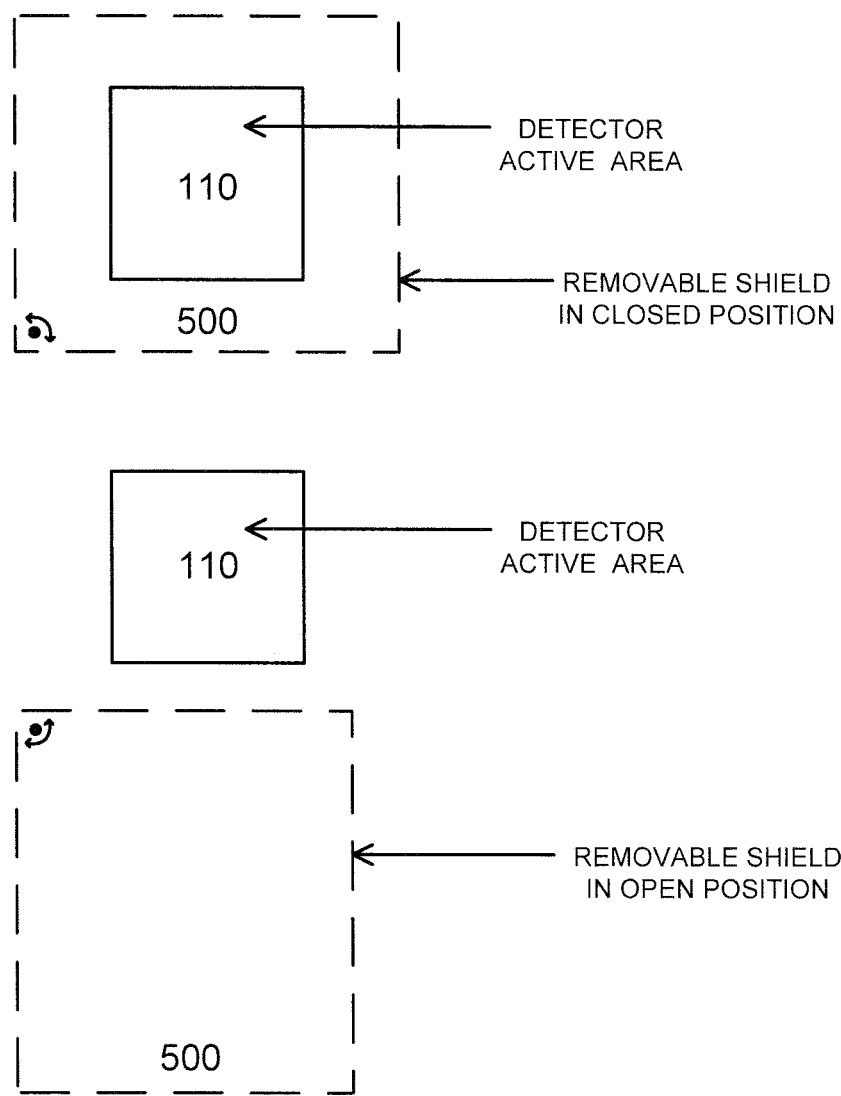
FIG. 8 is a diagram showing rotary motion of the detector shield of one embodiment of the present invention.
Figure 9:
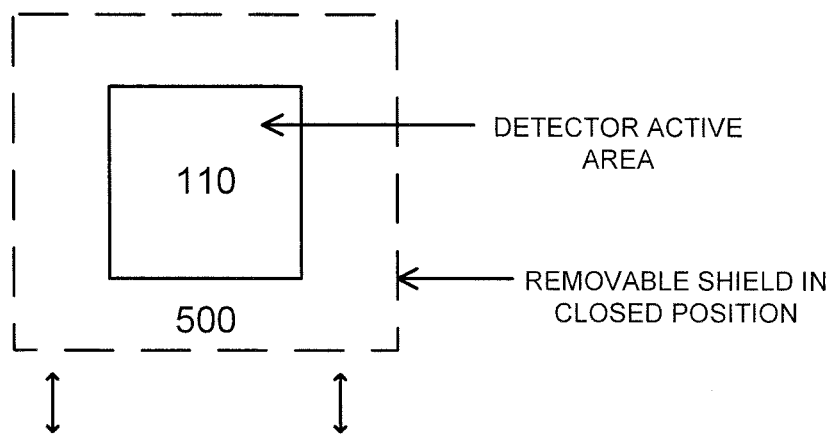
FIG. 9 is a diagram showing linear motion of the detector shield of one embodiment of the present invention.
Figure 9:
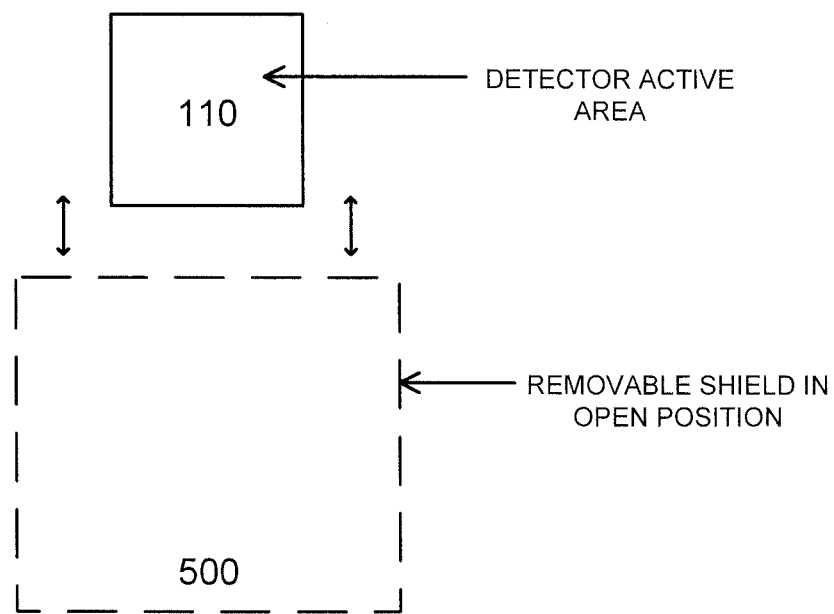
Figure 10:
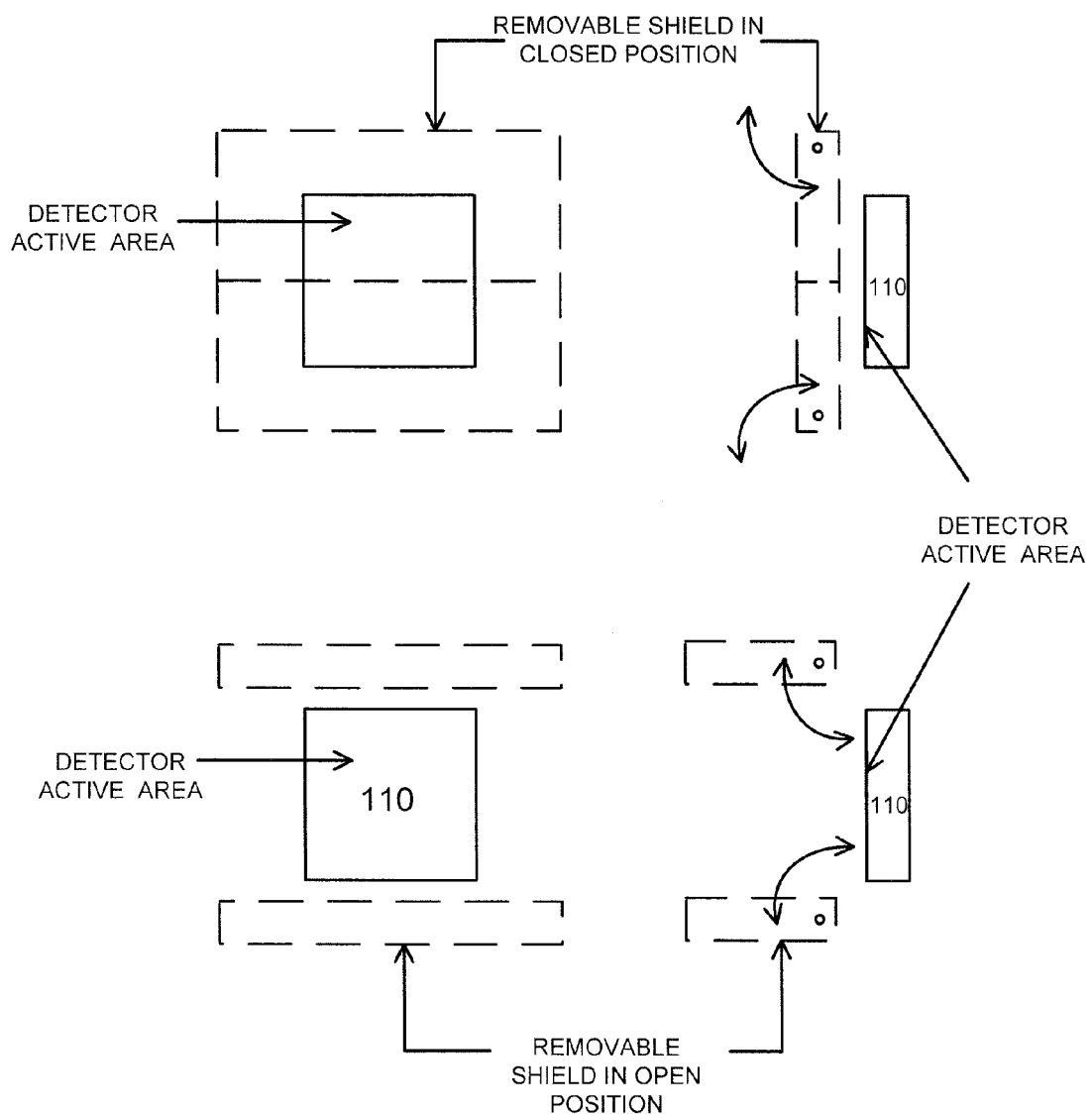
FIG. 10 is a diagram showing dual panel motion of the detector shields of one embodiment of the present invention.

The active surface of x-ray detector 110 can also be protected by one or more moveable shields made of high-density materials. The moveable shields can be a circular, elliptical, square, rectangular, quadrilateral, trapezoid, pentagon, hexagon, septagon, octagon or other shape. Prior to imaging, an actuator moves the moveable shields to expose x-ray detector 110 to the incoming x-ray radiation from x-ray source 10. After imaging is complete or during suspension of imaging, the moveable shields are returned to the protective position and radiation source 2 can be activated. The motion of the moveable shields should be rapid, and preferably less than 0.3 seconds, so as to allow a short elapsed time between imaging and the delivery of the radiation therapy. Alternatively, the opening or closing time for the moveable shields can be 0.1 s, 0.2 s, 0.3 s, 0.4 s, 0.5 s, 0.6 s, 0.7 s 0.8 s, 0.9 s, 1 s, 1.25 s, 1.5 s, 1.75 s, 2 s, 3 s, 4 s, 5 s, 6 s, 7 s, 8 s, 9 s, 10 s or any period in between such periods or any range of periods in between such periods. Since the active area of x-ray detector 110 used with x-ray source 10 is relatively small, the mechanical actuators can be arranged to move the moveable shields rapidly. In addition, a smaller detector is easier to shield eliminating the use of large or heavy shield associated with larger detectors. The active area of x-ray detector 110 can be square or rectangular shaped. The sides of x-ray detector 110 can have a length of 5 cm, 6 cm, 7 cm, 8 cm, 9 cm, 10 cm, 10.5 cm, 11 cm, 12 cm or any length in between such lengths or any range of lengths in between such lengths. FIG. 8 is a diagram showing rotary motion of the detector shield of one embodiment of the present invention. Detector shield 500 can rotate about an axis that is normal to the plane of the face of x-ray detector 110. Rotational movement allows for rapid opening or closing of the detector shield. Alternatively, one, two, three, four or more detector shields can be added that rotate about the same axis. With multiple detector shields, the time for opening and closing is further enhanced. FIG. 9 is a diagram showing linear motion of the detector shield of one embodiment of the present invention. Detector shield 500 slides in a plane parallel to the face of x-ray detector 110. FIG. 10 is a diagram showing dual panel motion of the detector shields of one embodiment of the present invention. Two detector shields can be used. Each detector shield rotates about an axis parallel to the plane of the face of x-ray detector 110.

The area of the circular active area of collimation grid 90 is preferably larger than the area of multi-detector array 110. Thus the axes of the x-ray pencil beams 100 emitted from the respective apertures 140 of collimation grid 90 all converge toward the multi-detector array 110 while each individual x-ray pencil beam 100 diverges, or spreads, as would a flashlight beam to cover the face of the multi-detector array 110.

Image reconstruction can be utilized to obtain high quality x-ray images. The output of the multi-detector array is preferably not applied directly to the luminance input of a video monitor. Instead, digitized intensity data for each image pixel are stored in a discrete address in a "frame store buffer". More than one such buffer may be used in certain applications. Pixel addresses within the buffer can be randomly accessed and the intensity value can be manipulated mathematically. This function has application in applying various image enhancement algorithms and it allows for pixel assignment of the data from discrete segments of the detector array.

Figure 11:
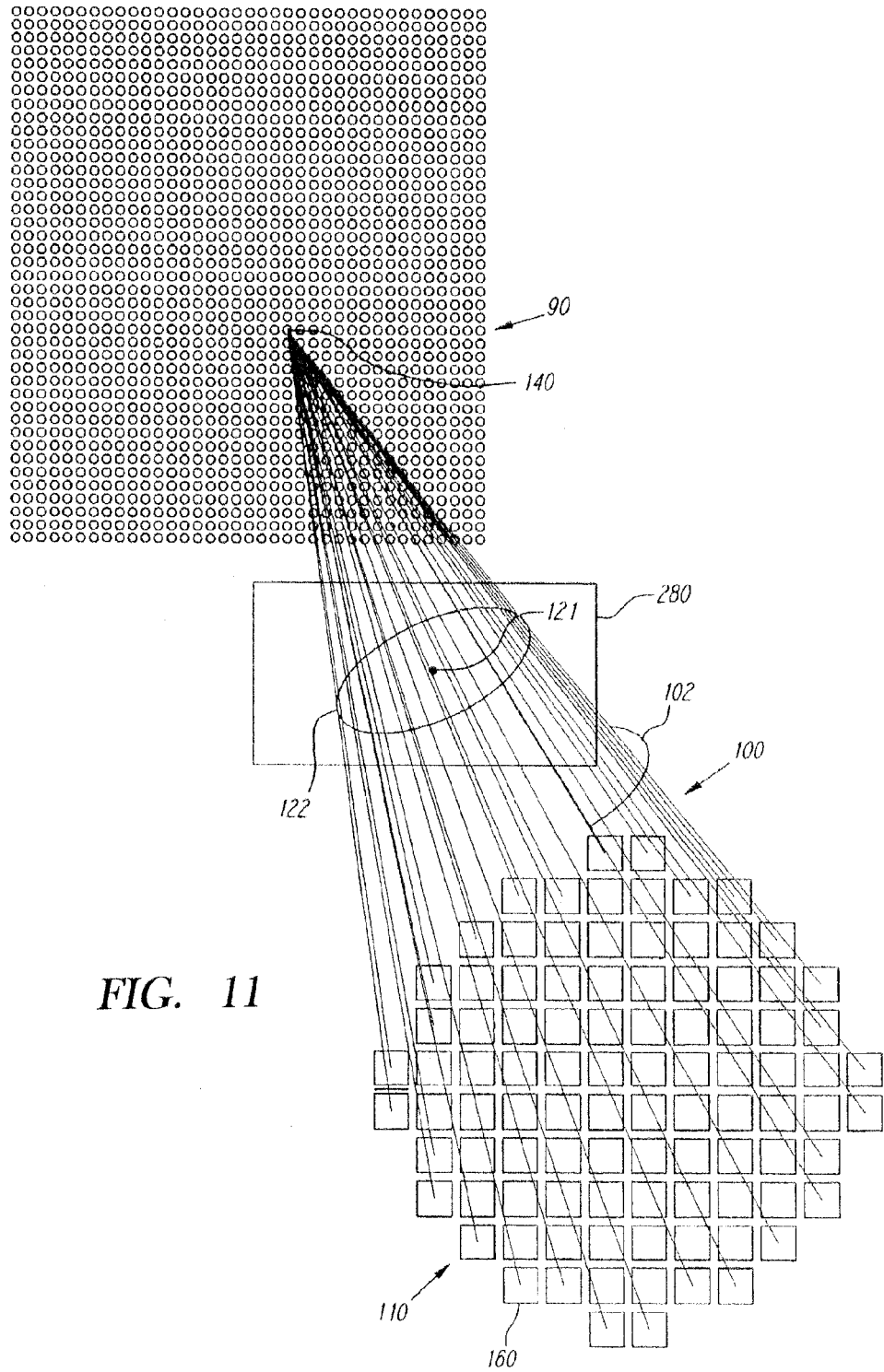
FIG. 11 is a diagram showing the divergence of a single x-ray pencil beam from an aperture to the multi-detector array and the intersection with an object at an object plane.

Referring to FIG. 11, this diagram illustrates the divergence of a single x-ray pencil beam 100 from aperture 140 to the multi-detector array and how it intersects an object 80 (not shown) at object plane 280. Image pixel 121 can be just one of the image pixels comprising the x-ray pencil beam intersection area 122 of object plane 280. A representative sample of the axes 102 of the x-ray micro-beams created by having a segmented array are also shown. In FIG. 11, x-ray pencil beam 100 is shown emitted through a single aperture 140 of collimator grid 90. X-ray pencil beam 100 as it exits aperture 140 can diverge forming a cone having a cross section the size of the aperture as it exits the aperture to a cross section covering the scintillators of the detector elements of the multi-detector array by the time it reaches 96 element multi-detector array 110. 96 element multi-detector array 110 can be positioned and designed such that the area of the cone of the x-ray beam 100 just covers the surface area of the multi-detector array 160 when the x-ray pencil beam 100 intersects the face of the multi-detector array.

As x-ray pencil beam 100 passes through object 80, information about object 80 can be detected by the multi-detector array 110 as x-ray intensity values. Because multi-detector array 110 is composed of 96 separate detector elements, each detector element 160 can detect only the intensity value for the particular x-ray micro-beam 101 of a segment of x-ray pencil beam 100 that it intersects with. The cross sectional shape and area of the x-ray micro-beams can correspond to the cross sectional area and shape as the input face of the detector elements. For example, if the input faces are square, the x-ray micro-beam can have a square cross section. The x-ray pencil beam 100 emitted from each aperture 140 on collimator grid 90 can therefore generate one group of 96 separate or discrete pieces of information (the intensity value at each detector element) about 96 areas of object 80 in the x-ray pencil beam's 100 path 122. The intensity information from each of the x-ray micro-beams can provide partial image pixel information which can be used to compile complete image pixel information for each image pixel in a desired plane of object 80.

Figure 12:
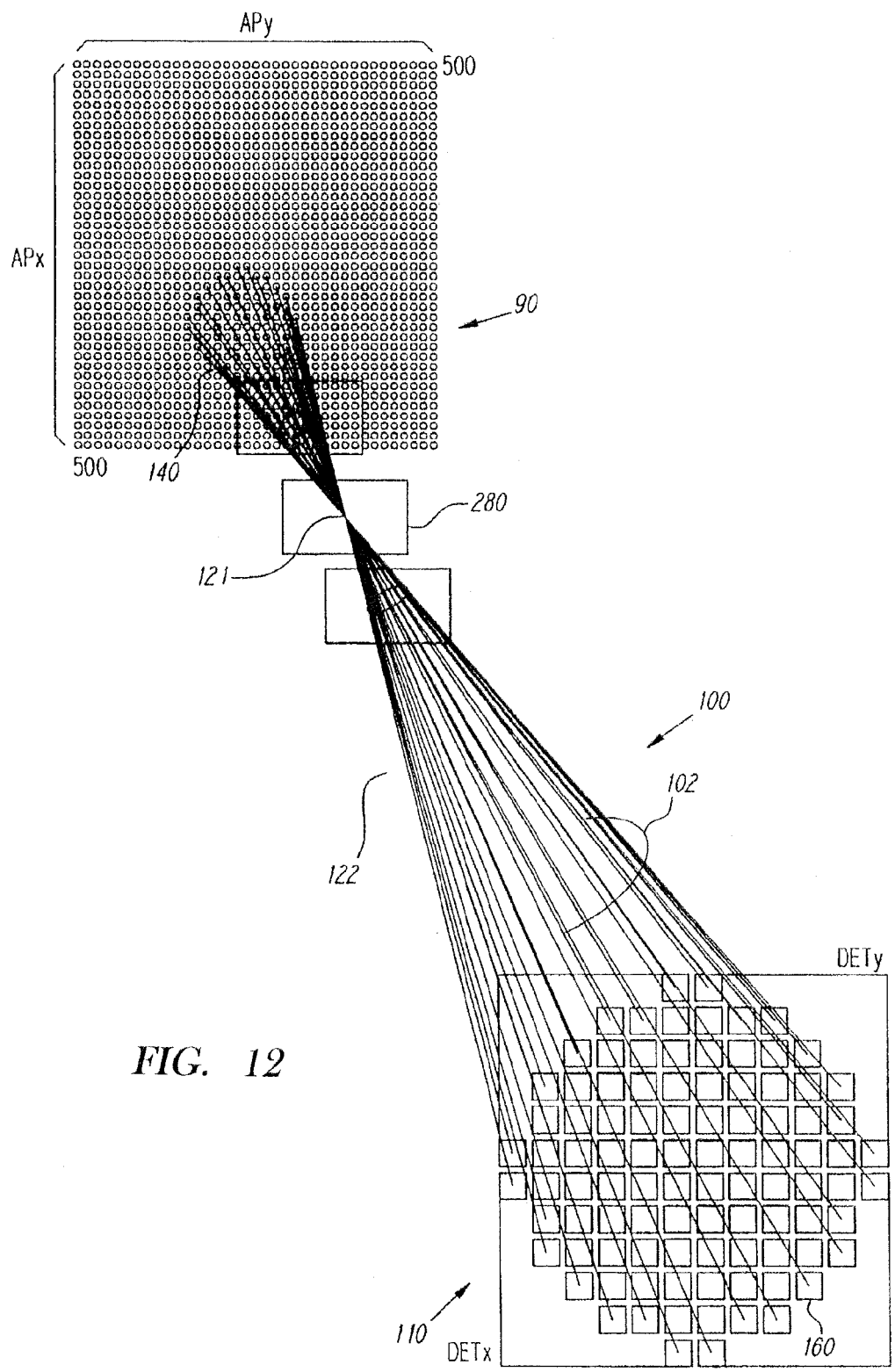
FIG. 12 is a diagram showing the axes of all of the x-ray micro-beams from all of the apertures that intersect a single image pixel in an object plane as they travel to the multi-detector array.

FIG. 12 illustrates the axes 102 of all of the x-ray micro-beams from all of the apertures 140 that intersect a single image pixel 121 in object plane 280 as they travel to the multi-detector array 110. This image pixel group of x-ray micro-beams can be ultimately processed to generate an image pixel on a video monitor. In one embodiment of the scanning-beam x-ray system, the apertures 140 on collimator grid 90 can generate x-ray pencil beams 100 in a predetermined pattern. As x-ray pencil beams 100 pass through an object, x-ray micro-beams 101 from adjacent and nearby apertures can intersect at, for example, point 121 (e.g. an image pixel) in the object. The intensity of each of these x-ray micro-beams 101 from these x-ray pencil beams 100 after they pass through the object can provide information about these intersecting points in the object. In this embodiment, each intersecting point on the object can therefore be considered a single-image "pixel" 121. In accordance with the techniques explained in more detail herein, each image pixel 121 can be mathematically reconstructed from the intensity information of the separate x-ray micro-beams 101 that were generated by the detector elements 160 for each of the emitted x-ray pencil beams 100 from, for example, the image pixel group of apertures that generated x-ray micro-beams whose axes passed through the object at that point, image pixel 121.

In this example, a corresponding pattern of data assignment is repeated as the scanning x-ray beam passes behind all of the pixels.

In the displayed image, with a sub-sampling ratio of 1:1, the numerical value of each image pixel is equal to the sum of "n" parts where "n" is the number of detectors in the multi-detector array 110 (in this example, n=9).

When constructed as shown in this example, the multi-detector array 110 together with the image reconstruction method selected, has the effect of fixing the working distance at which optimum focus is obtained and providing a plane of optimum focus.

The total area of the multi-detector array 110 should be large enough to intercept all of the x-rays in x-ray pencil beam 100 emanating from the collimation grid 90, to avoid exposing the patient to x-ray radiation which does not contribute to the image.

Outside of the plane of optimum spatial resolution, SO (280 in FIG. 6 and FIG. 11), spatial resolution will degrade. In some applications, degraded spatial resolution outside of the depth of field of the system may be seen as being advantageous because blurring of detail outside of the area of interest may tend to increase the perception of details within the area of interest.

A number of methods can be used to obtain a useable image from the data obtained as described above. A simple convolution method may be used. Two additional methods can be utilized for obtaining maximal resolution and sensitivity from the captured data, the multi-image convolution method and the multi-output convolution method. An advantage of the multi-image convolution method over the multi-output convolution method is that the former allows the plane of optimum focus to be selected in software after the data is captured while the latter does not. The latter method, however, may be performed quicker where timing is a limitation.

The scanning-beam imaging system described herein can be used to generate a set of sequential planar images which can then be used to form a tomograph or a three dimensional display of the object 80. An image set can be analyzed to produce a three dimensional image consisting of a series of images at various depths by re-analyzing the data set with various values corresponding to planes of interest in the object 80.

An alternative image reconstruction method can be employed to reconstruct images along multiple focal planes. This image reconstruction method is referred to as m,n image reconstruction. It will be noted that there are numerous planes parallel to the source plane and detector plane where multiple beams pass through regularly-spaced points in the plane. These planes are referred to as focal planes or image planes. The regularly-spaced points are referred to as image pixels. Each focal or image plane comprise characteristics which differ from other focal planes, including distance from the source, spacing of image pixels, and size of the image plane. Due to partial image reconstruction around the perimeter of the image, the number of fully reconstructed image pixels is slightly lower than the above number and the total number of fully and partially reconstructed image pixels is slightly higher than the above number. The m,n image reconstruction method is more flexible than the previously described reconstruction methods. As described, m,n image reconstruction can generate a wide variety of focal planes at numerous positions between the source and detector planes. Many of the focal planes have a small pitch between image pixels which can be used to produce images with high spatial resolution.

The ability to reconstruct a wide variety of focal planes can be used to move the focal plane with respect to the source and detector by simply selecting a suitable image plane near the region of interest of the object to be imaged.

The m,n image reconstruction method can also be used to increase the effective depth of field of an image by simultaneously reconstructing multiple focal planes around a region of interest. The reconstructed planes can be combined to produce a single image with high spatial resolution over a larger range of distances from the x-ray source plane. The multiple reconstructed planes can be combined, for example, by adding together only the high spatial frequency components from each reconstructed plane.

Under one embodiment of the present invention, the imaging system utilizes the sub-sampling method to process the detected information. The sub-sampling method can be employed in a reverse geometry scanning beam x-ray system utilizing a sub-sampling ratio of 9:1 with a multi-detector array including ninety-six detector elements arranged in a pseudo-circle. The multi-image convolution method, the multi-output convolution method, m,n image reconstruction method and sub-sampling method is described more fully in U.S. Pat. No. 5,651,047 entitled "Maneuverable and Locateable Catheters" which has been incorporated herein by reference in its entirety.

To generate an image pixel, the processed x-ray intensity values detected by the multi-detector array 110 for each x-ray micro-beam passing through that image pixel IP are summed and output to a video monitor. For image reconstruction using a sub-sampling ratio of 1:1 each logical detector element of the logical array is capable of providing information about each image pixel in the object. For image reconstruction with a sub-sampling ratio of x:1, where x is a number greater than 1, less than all of the logical detector elements are capable of contributing information about a particular image pixel. The actual number capable of contributing information will depend on the particular sub-sampling ratio selected. With a sub-sampling ratio of 9:1, only 16 logical detector elements of the 144 logical detector element logical array will provide information about any particular image pixel.

In the sub-sampling method with a sub-sampling ratio of 9:1, the logical array can include sixteen virtual detectors. The virtual detectors can each include 9 logical detectors arranged in a 3 by 3 array. Alternatively, if a sub-sampling ratio of 4:1 were used, there would be 36 virtual detectors, each including 4 logical detector elements. Using a sub-sampling ratio of 1:1 there would be 144 virtual detectors each including 1 logical detector element.

Each of the 16 logical detector elements used to reconstruct a single image pixel using a sub-sampling ratio of 9:1 can be in different virtual detectors. Each virtual detector contributes partial image pixel information for nine different image pixels. Complete image pixel information is obtained by combining the information from the logical detectors in the same virtual array location from all 16 virtual detectors.

Additional image reconstruction methods and techniques can be utilized to generate information for a wide variety of planes and slices at numerous positions between the source and detector. These methods and techniques are described more fully in commonly owned U.S. Pat. Nos. 6,178,223 and 6,181,764, entitled "Image Reconstruction Method and Apparatus" and "Image Reconstruction for Wide Depth of Field Images," all of which are hereby incorporated herein by reference in their entirety.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A radiation therapy system for delivering radiation to a human patient comprising:
   a radiation therapy source for delivering radiation to a target in said human patient;
   a scanning beam x-ray source for providing x-ray photons directed to said target;
   an x-ray detector for measuring a number of said x-ray photons passing through said target and striking said detector;
   an image reconstruction processor coupled to said x-ray detector for producing an image based on said number of said x-ray photons passing through said target and striking said detector;
   a detector shield assembly for shielding said x-ray detector from said radiation from said radiation therapy source, configured to have a first position outside of all beam paths between said scanning beam x-ray source and active surface of said x-ray detector and a second position occluding all of said beam paths between said scanning beam x-ray source and said active surface of said x-ray detector; and
   a mechanical actuator coupled to said detector shield assembly for moving said detector shield assembly between said first position and said second position in less than 0.3 seconds.

2. The radiation therapy system of claim 1 wherein said x-ray detector is a photon counting detector.

3. The radiation therapy system of claim 1 wherein said mechanical actuator is configured to slide said detector shield assembly in a plane parallel to a face of said x-ray detector.

4. The radiation therapy system of claim 1 wherein said a mechanical actuator is configured to rotate said detector shield assembly about an axis normal to a plane of a face of said x-ray detector.

5. The radiation therapy system of claim 1 wherein said mechanical actuator is configured to rotate said detector shield assembly about an axis parallel to a plane of a face of said x-ray detector.

6. The radiation therapy system of claim 5 wherein said detector shield assembly further comprises a plurality of panels.

7. The radiation therapy system of claim 1 wherein said x-ray detector is located at least 1.5 m away from said target.

8. The radiation therapy system of claim 1 wherein the angle between the line from said radiation source to said target and the line from a center of said x-ray detector to said target is fixed to be less than 40 degrees.

9. A method for delivering radiation therapy to a human patient comprising:
   scanning an electron beam over a target in a predetermined pattern;
   producing x-ray photons from a plurality of discrete locations on said target;
   directing said x-ray photons towards an object in said patient;
   measuring an amount of x-ray photons striking a detector located at least 1.5 m from said human patient;
   producing an image of said object based on said amount of x-ray photons striking said detector;
   directing radiation from a radiation therapy source towards said object;
   moving a detector shield into a first position occluding all beam paths between said scanning beam x-ray source and active surface of said x-ray detector prior to directing said radiation from said radiation therapy source towards said object; and
   moving said detector shield into a second position outside of all beam paths between said scanning beam x-ray source and said active surface of said x-ray after directing said radiation from said radiation therapy source towards said object detector in less than 0.3 second.

10. The method of claim 9 further comprising:
counting a number of said x-ray photons striking said detector.

11. The method of claim 9 further comprising:
sliding a detector shield in a plane parallel to a face of said detector to cover said detector prior to directing radiation from said radiation therapy source towards said object.

12. The method of claim 9 further comprising:
rotating a detector shield about an axis normal to a plane of a face of said detector to cover said detector prior to directing radiation from said radiation therapy source towards said object.

13. The method of claim 9 further comprising:
rotating a detector shield about an axis parallel to a plane of a face of said detector to cover said detector prior to directing radiation from said radiation therapy source towards said object.

* * * * *